US 6,685,962 B2

(12) United States Patent
Friedman et al.

(10) Patent No.: US 6,685,962 B2
(45) Date of Patent: Feb. 3, 2004

(54) GASTRORETENTIVE CONTROLLED RELEASE PHARMACEUTICAL DOSAGE FORMS

(75) Inventors: Michael Friedman, Jerusalem (IL); Eytan Klausner, Jerusalem (IL); Eran Lavy, Maccabim (IL); Amnon Hoffman, Jerusalem (IL)

(73) Assignee: Yissum Research Development Company Of The Hebrew University Of Jerusalem (IL)

( * ) Notice: Subject to any disclaimer, the term of this patent is extended or adjusted under 35 U.S.C. 154(b) by 0 days.

(21) Appl. No.: 10/157,325

(22) Filed: May 29, 2002

(65) Prior Publication Data

US 2003/0021845 A1 Jan. 30, 2003

Related U.S. Application Data

(63) Continuation of application No. PCT/IL00/00774, filed on Nov. 20, 2000.

(30) Foreign Application Priority Data

Nov. 29, 1999 (IL) .................................................. 133196

(51) Int. Cl.[7] .................................................. A61K 9/52
(52) U.S. Cl. ........................ 424/457; 424/451; 424/452; 424/458; 424/459; 424/460; 424/467; 424/462; 424/484; 424/485; 424/486; 424/487; 424/488; 424/483; 424/480; 424/491; 424/493; 424/494; 424/495
(58) Field of Search ................................ 424/484, 485, 424/486, 487, 488, 489, 490, 491, 492, 493, 494, 495, 496, 497, 498, 499, 500, 464, 465, 466, 468, 469, 474, 451, 452, 456, 457, 458, 459, 460, 461, 462, 463

(56) References Cited

U.S. PATENT DOCUMENTS

| 3,574,820 A | 4/1971 | Johnson et al. |
| 4,207,890 A | 6/1980 | Mamajek et al. |
| 4,434,153 A | 2/1984 | Urquhart et al. |
| 4,735,804 A | 4/1988 | Caldwell et al. |
| 4,758,436 A | 7/1988 | Caldwell et al. |
| 4,767,627 A | 8/1988 | Caldwell et al. |

(List continued on next page.)

FOREIGN PATENT DOCUMENTS

EP   0 656 204 A1   6/1995

OTHER PUBLICATIONS

Khosla, R., "The effect of tablet size on the gastric emptying of non-disintegrating tablets," International Journal of Pharmaceutics, 62 (1990), pp. R9–R11.

(List continued on next page.)

Primary Examiner—Thurman K. Page
Assistant Examiner—Liliana Dinola-Baron
(74) Attorney, Agent, or Firm—Lerner, David, Littenberg, Krumholz & Mentlik, LLP

(57) ABSTRACT

Pharmaceutical gastroretentive drug delivery systems for the controlled release of an active agent in the gastrointestinal tract are disclosed, which comprise: (a) a single- or multi-layered matrix comprising a polymer that does not retain in the stomach more than a conventional dosage form selected from (1) degradable polymers that may be hydrophilic polymers not instantly soluble in gastric fluids, enteric polymers substantially insoluble at pH less than 5.5 and/or hydrophobic polymers and mixtures thereof; (2) non-degradable polymers; and any mixtures of (1) and (2); (b) a continuous or non-continuous membrane comprising at least one polymer having a substantial mechanical strength; and (c) a drug; wherein the matrix when affixed or attached to the membrane prevents evacuation from the stomach of the delivery system for a period of time of from about 3 to about 24 hours.

35 Claims, 5 Drawing Sheets

U.S. PATENT DOCUMENTS

| | | |
|---|---|---|
| 5,002,772 A | 3/1991 | Curatolo et al. |
| 5,047,464 A | 9/1991 | Pogany et al. |
| 5,217,712 A | 6/1993 | Pogany et al. |
| 5,443,843 A | 8/1995 | Curatolo et al. |
| 5,651,985 A | 7/1997 | Penners et al. |
| 5,840,332 A * | 11/1998 | Lerner et al. ............... 424/464 |

OTHER PUBLICATIONS

Remington, The Science and Practice of Pharmacy, 19th ed., vol. 2, p. 1398. 1990.

Handbook of Pharmaceutical Excipients, 2nd ed., The Pharmaceutical Press, p. 230. 1993.

Bode, H. et al., "Investigation of nifedipine absorption in different regions of the human gastrointestinal (GI) tract after simultaneous administration of $^{13}C-$ and $^{13}C-$nifedipine," Eur. J. Clin. Pharmacol (1996) 50:195–201.

Physician's Desk Refernce, PDR 50 ed., 1996, p. 2097.

Handbook of Biodegradable Polymers, Domb, Kost, Weisman, eds., 1997, Harwood Academic Publishers.

* cited by examiner

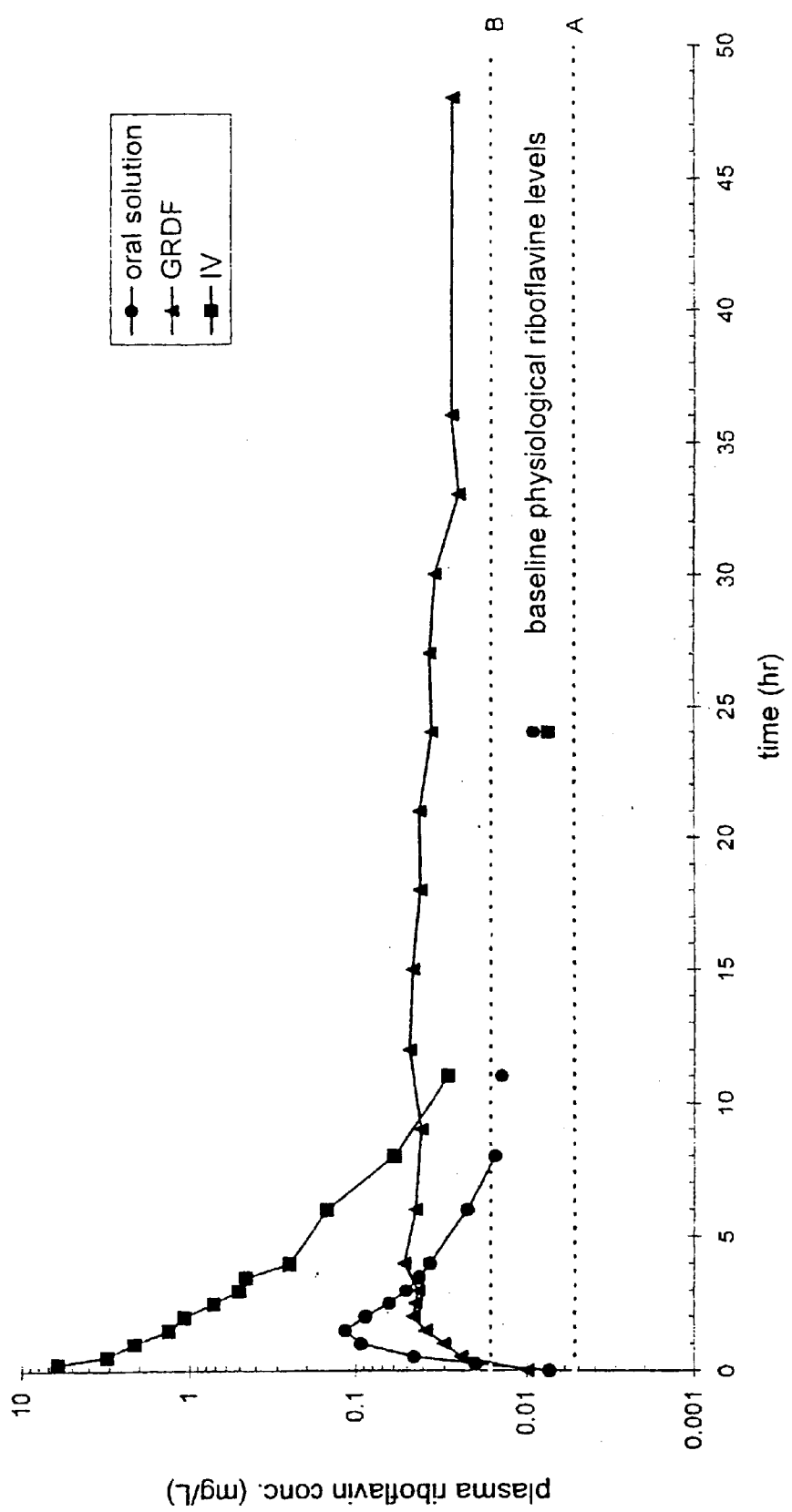

GASTRORETENTIVE CONTROLLED RELEASE PHARMACEUTICAL DOSAGE FORMS

CROSS-REFERENCE TO RELATED APPLICATIONS

The present application is a continuation of International Application No. PCT/IL00/00774, which was filed on Nov. 20, 2000, in the English language.

FIELD OF THE INVENTION

The present invention relates to pharmaceutical drug delivery systems for the controlled release of active agents having a narrow absorption window in the gastrointestinal tract, i.e. are usually absorbed in the duodenum and/or jejunum. The invention also relates to the uses of these controlled release delivery systems in the treatment of gastrointestinal-associated disorders and diseases in mammals.

BACKGROUND OF THE INVENTION

Pharmaceutical dosage forms which retain in the stomach for a prolonged period of time after oral administration, and release the active ingredient in a controlled manner are important for delivery of a wide variety of drugs. Various pharmaceutical controlled release drug delivery systems with prolonged gastric retention time have been described in the literature, which involve different technologies.

The advantages of using drug delivery systems are many. Of major importance in controlled drug therapy is the improved efficiency in treatment. Controlled drug therapy reduces the required frequency of administration, and single doses at periodic intervals are sufficient, resulting in improved patient compliance.

However, conventional controlled release drug delivery systems have only limited use for (1) drugs having a narrow absorption window in the gastrointestinal tract, i.e. are absorbed in the duodenum and/or jejunum; (2) local treatment of proximal parts of the gastrointestinal tract (stomach and/or duodenum); and (3) drugs which degrade in the colon. To enable the improved therapy in these cases, a gastroretentive pharmaceutical dosage form should be developed. After oral administration, such gastroretentive dosage form should retain in the stomach and release the drug in a controlled and prolonged manner. Examples of gastroretentive dosage forms are floating dosage forms and dosage forms that expand, swell or unfold in the stomach.

The rationale for developing expandable drug delivery systems is based on the nature of the pyloric antrum that, by means of antiperistaltic motion, retropels large bodies away from the pylorus back to the fundus and body of the stomach, thus prolonging their gastric retention time (GRT). Such dosage forms should preferably be designed to undergo biodegradation or disintegration, to enable their evacuation from the stomach.

U.S. Pat. No. 3,574,820 teaches the use of a gelatin matrix which hydrates in the stomach, gels, swells and cross-links with N-acetyl-homocysteine thiolactone to form a matrix too large to pass through the pylorus.

U.S. Pat. No. 4,207,890 discloses a drug dispensing device which comprises a collapsed, expandable imperforate envelope, made of a non-hydratable, body fluid and drug-permeable polymeric film, which contains the drug, and an expanding agent also contained within the polymeric envelope which, when in contact with body fluids, causes the envelope to expand to a volume such that the device is retained in the stomach.

U.S. Pat. No. 4,434,153 describes a device comprised of a matrix formed of a hydrogel that absorbs and imbibes fluid from the stomach, expands and swells, in order to retain in the stomach for an extended period of time, and a plurality of tiny pills dispersed throughout the matrix, having a drug-containing core and a fatty acid and wax wall surrounding the core A significant disadvantage of the devices of the above publications is that they appear to ignore natural contractions of the stomach which may contribute to a rapid diminishing of size, leading to early removal of the device from the stomach. These devices lack the mechanical strength required to withstand the natural mechanical activity, that includes contractions of the stomach.

U.S. Pat. Nos. 4,767,627, 4,735,804 and 4,758,436 present dosage forms of various geometries: continuous solid stick; tetrahedron; planar disc; multi-lobed flat device; and ring. The devices are compressible to a size suitable for swallowing, and are self-expandable to a size which prevents passage through the pylorus. They are sufficiently resistant to forces of the stomach to prevent rapid passage through the pylorus for a pre-determined period of time and erode in the presence of gastric juices. The devices are homogenous, namely they contain the same polymer constitution in different areas of the device. The tetrahedron presented in U.S. Pat. No. 4,735,804 is homogenous in its four lobes, which are attached to each other by a polymeric matrix.

The medicaments are incorporated into the device as a liquid solution or suspension, which may necessitate the addition of mentioned preservatives or buffering agents. Alternatively, the controlled release drug module may be tethered or glued to the device.

U.S. Pat. Nos. 5,002,772 and 5,443,843 disclose an oral drug delivery system having a delayed gastrointestinal transit, which releases the drug/s contained therein in a controlled manner and which in their expanded form resist gastrointestinal transit. These delivery systems comprise one or more retention arms as a non-continuous compressible element, and an attached controlled release drug-containing device. The preferred configuration is a coil or a spiral. These systems must comprise at least two distinct parts (at least one retention arm and a controlled release device).

U.S. Pat. Nos. 5,047,464 and 5,217,712 describe a system comprising bio-erodible, thermoset, covalently cross-linked, poly(ortho) ester polymers, which expand from a compressed state upon delivery thereof. The acidic environment of the stomach eventually results in the degradation of the polymers within the system, thus permitting its removal from the stomach. The system is characterized by high resiliency.

Finally, U.S. Pat. No. 5,651,985 describes a system devised from a mixture of polyvinyl-lactams and polyacrylates which are characterized by their high degree of swelling in the stomach resulting in its retention in the stomach for a prolonged period of time.

Notwithstanding the developments in gastric retention devices, known devices still suffer many drawbacks, and there is need for yet improved delivery systems. The present invention is aimed at such improved devices, which would overcome the drawbacks of known devices.

It is therefore an object of the invention to provide a controlled-release drug delivery system that would retain in the stomach for a sufficient period of time, while releasing the active drug therefrom.

This and other objects of the invention would become clearer as the description proceeds.

SUMMARY OF THE INVENTION

The present invention relates to a pharmaceutical gastroretentive drug delivery system for the controlled release of an active agent in the gastrointestinal tract, which system comprises:

a) a single- or multi-layered matrix having a two- or three-dimensional geometric configuration comprising a polymer that does not retain in the stomach more than a conventional dosage form, said polymer selected from:
   (1) a degradable polymer selected from:
      (i) a hydrophilic polymer which is not instantly soluble in gastric fluids;
      (ii) an enteric polymer substantially insoluble at pH less than 5.5;
      (iii) a hydrophobic polymer; and
      (iv) any mixture of at least two polymers as defined in (i), (ii) or (iii);
   (2) a non-degradable; and
   (3) a mixture of at least one polymer as defined in (1) with at least one polymer as defined in (2);
b) a continuous or non-continuous membrane, that does not retain in the stomach more than a conventional dosage form, affixed or attached to said matrix, said membrane comprising at least one polymer having a substantial mechanical strength; and
c) a drug, which may be in a particulate form or optionally contained within a drug-containing means; said drug or drug contained within said drug-containing means being embedded in a layer of said matrix, or being entrapped between at least two layers of said matrix, or being attached to said delivery system,
   wherein said matrix when affixed or attached to said membrane prevents evacuation from the stomach of said delivery system for a period of time of from about 3 to about 24 hours.

The delivery system of the invention may further comprise a shielding layer covering at least one face of said matrix, optionally covering all or part of said membrane, said shielding layer comprising a polymer that does not retain in the stomach more than a conventional dosage form, said polymer being selected from (a) a hydrophilic polymer which is not instantly soluble in gastric fluids; (b) an enteric polymer substantially insoluble at pH less than 5.5; (c) a hydrophobic polymer; and (d) any mixture of at least two polymers as defined in any of (a), (b) or (c).

The drug contained in the delivery system of the invention may be in the form of raw powder, or a powder soluted, dispersed or embedded in a suitable liquid, semisolid, micro- or nanoparticles, micro- or nanospheres, tablet, capsule or a suitable specific two- or three-dimensional matrix.

The delivery system of the invention may further comprise a suitable plasticizer, which may be contained in any of the components of the delivery system. The plasticizer is preferably selected from the group consisting of an ester selected from phthalate esters, phosphate esters, citrate esters, fatty acid esters and tartarate esters, glycerine and glycol derivatives, and sorbitol. The plasticizer is preferably contained in the shielding layer.

In addition, the delivery system of the invention may further comprise at least one gas-forming agent. The gas-forming agent is preferably a liquid gas- forming agent which boils at body temperature or a solid gas-forming agent, preferably a pharmaceutically acceptable carbonate.

In a particular embodiment, the delivery system of the invention may additionally comprise an anti-adhering layer affixed to at least one outer face thereof. The anti-adhering layer preferably comprises a pharmaceutically acceptable cellulose or derivative thereof, silicate or an enteric polymer substantially insoluble at pH less than 5.5. In particularly preferred embodiments the said anti-adhering layer comprises microcrystalline cellulose.

The hydrophilic polymer comprised in the delivery system of the invention may be selected from the group consisting of a protein, a polysaccharide, a polyacrylate, a hydrogel, polyvinyl alcohol, polyvinyl pyrrolidone, and derivatives of such polymers.

The enteric polymer comprised in the delivery system of the invention may be selected from the group consisting of shellac, cellulose acetate phthalate, hydroxypropyl methylcellulose phthalate, hydroxypropyl methylcellulose acetate succinate and methylmethacrylate-methacrylic acid copolymers, preferably having a ratio of ester to free carboxylic groups of 2:1.

In a preferred embodiment, the delivery system of the invention comprises a shielding layer which comprises a mixture of said hydrophilic polymer and said enteric polymer and optionally further comprises s plasticizer. In such embodiments, the said hydrophilic polymer is preferably cross-linked with a suitable cross-linking agent particularly with glutaraldehyde. The hydrophilic polymer is preferably an enzymatically hydrolyzed cross-linked gelatin or a derivative thereof. The said enteric polymer is preferably methylmethacrylate-methacrylic acid copolymer having a ratio of ester to free carboxylic groups of 2:1. A particularly preferred plasticizer is glycerine.

In further specific embodiments, the hydrophobic non-degradable polymer comprised in the delivery system of the invention is selected from the group consisting of ethylcellulose, a copolymer of acrylic acid and methacrylic acid esters, having from about 5 to 10% functional quaternary ammonium groups, polyethylene, polyamide, polyvinylchloride, polyvinyl acetate and any mixtures thereof.

In yet a further particular embodiment, the membrane of the delivery system of the invention comprises hydrophobic non-degradable polymer/s, hydrophobic degradable polymer/s, or mixtures thereof. Preferably, the said membrane is comprised of a mixture of 1-poly(lactic acid) (1-PLA) and ethylcellulose at a ratio of 9:1, respectively.

The delivery system of the invention is suitable for the delivery of drugs having a narrow absorption window in the gastrointestinal tract. Such drugs may be therapeutic nucleic acids or amino acid sequences, nucleic acids or amino acid derivatives, peptidomimetic drugs, antibiotics, therapeutic ions, vitamins, bronchodilators, anti-gout agents, an anti-hypertensive agents, diuretic agents, anti-hyperlipidemic agents or ACE inhibitors.

The delivery system may also be particularly suitable for the delivery of drugs intended for local treatment of the gastrointestinal tract. Such drug may be anti-tumor agents, histamine (H2) blockers, bismuth salts, synthetic prostaglandins or antibiotic agents.

In addition, the delivery system of the invention may be suitable for the delivery of drugs that degrade in the colon, for example metoprolol.

The delivery system of the invention is particularly useful for the treatment of gastrointestinal associated disorders selected from peptic ulcer, nonulcer dyspepsia, Zollinger-Ellison syndrome, gastritis, duodenitis and the associated ulcerative lesions, stomach or duodenum neoplasms.

The delivery system of the invention may have the form of a disc, multi-lobed configuration, a triangle or a quadrangle, and may be planar or non-planar.

Further, the delivery system of the invention may be folded into a suitable capsule. Thus, in a further embodiment the invention also relates to a capsule containing a delivery system of the invention.

DESCRIPTION OF THE FIGURES

The invention will be described in more detail on hand of the following drawings, in which:

FIG. 5 shows the effect of mode of administration of 100 mg riboflavin-5-phosphate on mean riboflavin plasma concentrations in dogs. Drug given either as oral solution or gastroretentive dosage form (GRDF) (6 dogs). Concentrations between the dotted lines A and B represent baseline physiological riboflavin levels.

DETAILED DESCRIPTION OF THE INVENTION

Figure 1:
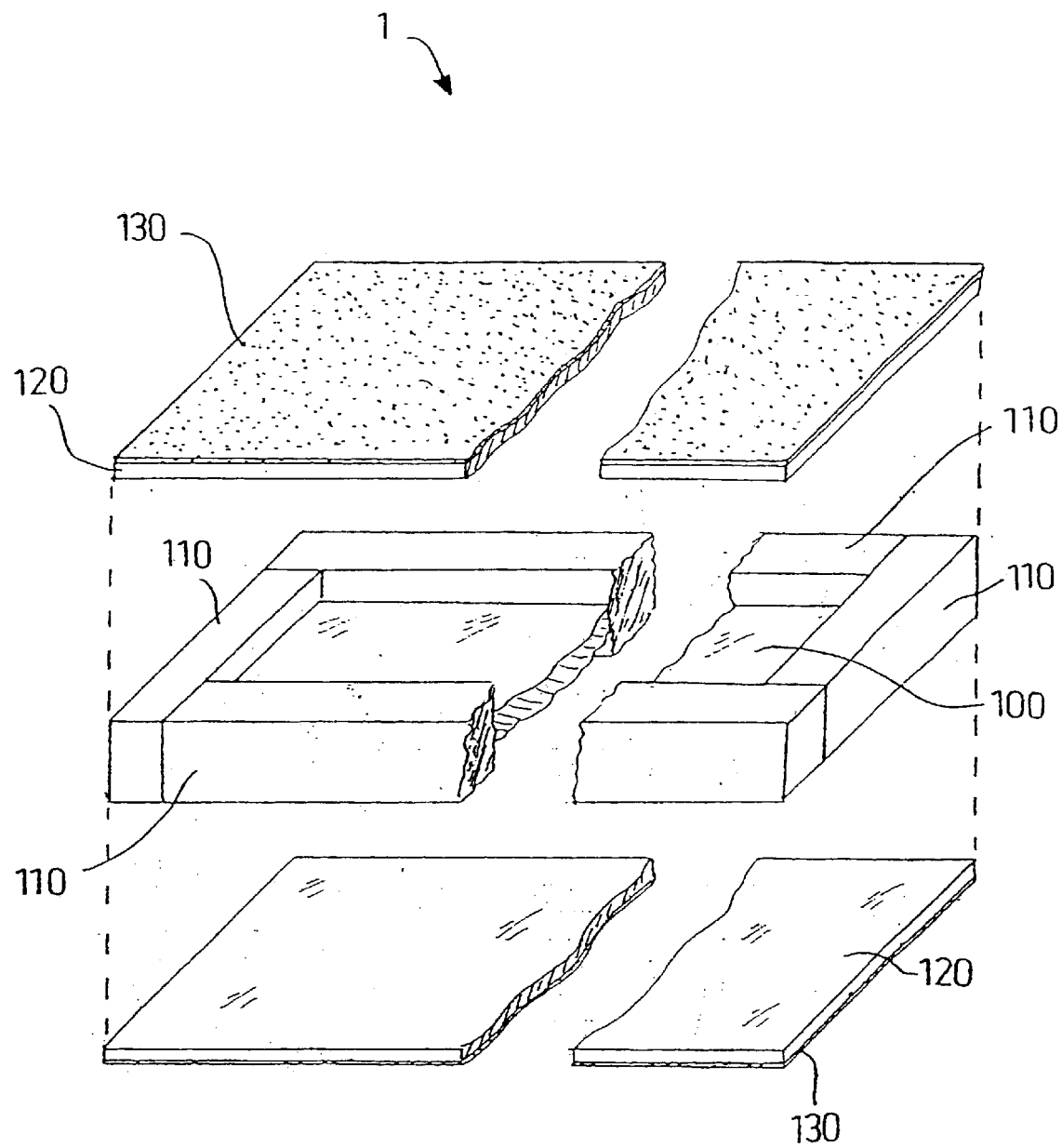
FIG. 1 is a partially fragmented exploded perspective view of an embodiment of a device according to the present invention.

Prolonged gastroretentive pharmaceutical dosage forms for releasing a drug in a controlled manner, such as that of the present invention, may provide many therapeutic benefits. One application in which the gastroretentive controlled delivery device of the invention may be advantageous is the administration of drugs having a narrow absorption window. These drugs are usually absorbed in limited segments of the upper parts of the gastrointestinal tract (most often in the duodenum and jejunum). In addition, many of these drugs are absorbed by active transport systems in the aforementioned upper parts of the gastrointestinal tract, or are poorly soluble at intestinal medium pH. It has been shown that prolonged duodenal delivery of drugs having a narrow absorption window enhances their bioavailability and evidently their therapeutic effect. One example for such an enhancement is the improved bioavailability and therapy of levodopa, infused directly into the duodenum.

Another application in which use of a prolonged gastroretentive drug delivery system may be advantageous is local treatment of diseases of the stomach or duodenum. Targeting the drug to the pathological tissue is usually preferable for treatment of localized disorders, as the concentration of the drug attained in the diseased tissue or organ is higher than its systemic concentration, resulting in enhanced effectiveness of the drug in the target organ or tissue, with reduced systemic side effects.

Gastroretentive delivery systems like the delivery system of the invention are also suitable for veterinary use, for the treatment of mammals, particularly domesticated animals and pets.

The basic concept underlying the delivery system of the present invention is the provision of a combination system, comprising at least two components, namely the matrix and the membrane affixed or attached thereto. Taken separately, neither the matrix nor the membrane would retain in the stomach more than a conventional dosage form. However, when the membrane is affixed or attached to the matrix, it prevents evacuation of the matrix for the desired period of time. At the same time, the matrix, when the membrane is affixed or attached thereto, prevents, for the desired period of time, the so termed "collapse" of the membrane, which would have led to its rapid evacuation from the stomach. The delivery system of the invention is so designed as to allow for its disintegration after the desired drug-release time, so that all of its components are evacuated from the stomach.

The present invention therefore relates to a pharmaceutical gastroretentive drug delivery system for the controlled release of an active agent in the gastrointestinal tract, which system comprises:

a) a single- or multi-layered matrix having a two- or three-dimensional geometric configuration comprising a polymer that does not retain in the stomach more than a conventional dosage form, said polymer selected from:
   (1) a degradable polymer selected from:
      i) a hydrophilic polymer which is not instantly soluble in gastric fluids;
      ii) an enteric polymer substantially insoluble at pH less than 5.5;
      iii) a hydrophobic polymer; and
      iv) any mixture of at least two polymers as defined in (i), (ii) or (iii);
   (2) a non-degradable; and
   (3) a mixture of at least one polymer as defined in (1) with at least one polymer as defined in (2);

b) a continuous or non-continuous membrane, that does not retain in the stomach more than a conventional dosage form, affixed or attached to said matrix, said membrane comprising at least one polymer having a substantial mechanical strength; and c) a drug, which may be in a particulate form or optionally contained within a drug-containing means; said drug or drug contained within said drug-containing means being embedded in a layer of said matrix, or being entrapped between at least two layers of said matrix, or being attached to said delivery system,
   wherein said matrix when affixed or attached to said membrane prevents evacuation from the stomach of said delivery system for a period of time of from about 3 to about 24 hours, preferably from about 8 to about 12 hours.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

By the term "does not retain in the stomach more than a conventional dosage form" is generally meant a polymer of such content, and optionally size, that does not retain in the fasted stomach for over 2 hours.

By the term "a polymer which is instantly soluble in gastric fluids" is generally meant a polymer which dissolves in the stomach within about 15 minutes from administration. Such polymers are, for example water-soluble polymers independent of the pH of the environment (for example Byco$^R$ or hydroxypropyl methylcellulose (HPMC)).

By the term "a polymer which is not instantly soluble in gastric fluids" is generally meant a polymer which will gradually dissolve in the stomach during its stay therein. Such polymers are, for example, cross-linked polymers which would dissolve at a rate of about 50% of the polymer over 24 hours.

By the term "having a substantial mechanical strength" is generally meant a polymer with Young's modulus of about 100–2000 Mpa and yield strength (at 0.5% offset) of about 2–25 Mpa, all measured using an Instron tensile tester at cross-head speed of 25 mm/min.

In order to control the mechanical strength, erosion and release characteristics of the drug or combinations of drugs contained in the delivery device, pharmaceutically acceptable, non-toxic fillers may optionally be added to the matrix, membrane or shielding layer. Examples of such fillers are starch, glucose, lactose, inorganic salts such as sodium or potassium chloride, carbonates, bicarbonates, sulfates, nitrates, silicates and alkali metals phosphates and oxides.

The membrane should control the gastroretentivity of the system by maintaining the system in its desired configuration for predetermined time. Evacuation of the system from the stomach should take place after the shielding layer (or if it does not exist then the matrix layer) undergoes biodegradation, bioerosion, dissolution or disintegration, thus enabling separation of the membrane to its smaller fragments or collapse of the membrane and inevitably the system in any other way.

The membranes used in the device of the invention have substantial mechanical strength. Such membranes may comprise, for example, cellulose ethers and other cellulose derivatives such as cellulose nitrate, cellulose acetate, cellulose acetate butyrate or cellulose acetate propionate; polyesters, such as polyethylene terephthalate, polystyrene, including copolymers and blends of the same; polylactides, including copolymers thereof with p-dioxanone, polyglycolides, polylactidglycolides; polyolefins, including polyethylene, and polypropylene; fluoroplastics, such as polyvinylidene fluoride and polytetrafluoroethylene, including copolymers of the same with hexafluoropropylene or ethylene; polyvinylchloride, polyvinylidene chloride copolymers, ethylene vinyl alcohol copolymers, polyvinyl alcohols, ammonium-methacrylate copolymers and other polyacrylates and polymethacrylates; polyacrylonitriles; polyurethanes; polyphthalamides; polyamides; polyimides; polyamide-imides; polysulfones; polyether sulfones; polyethylene sulfides; polybutadiene; polymethyl pentene; polyphenylene oxide (which may be modified); polyetherimides; polyhydroxyalkanoates; tyrosine derived polyarylates and polycarbonates including polyester carbonates, polyanhydrides, polyphenylene ethers, polyalkenamers, acetal polymers, polyallyls, phenolic polymers, polymelamine formaldehydes, epoxy polymers, polyketones, polyvinyl acetates and polyvinyl carbazoles.

In one preferred example, the membrane comprises a mixture of 1-poly(lactic acid) (1-PLA) and ethylcellulose, at a ratio of 9:1, respectively.

The membrane may contain, or be replaced by a suitable inert metal, e.g. titanium, or inert metal alloys, incorporated into the delivery system of the invention. Such metals or metal alloys serve in preventing the device from rapidly diminishing upon administration.

In a preferred embodiment, the gastroretentive delivery device of the invention may further comprise a shielding layer covering at least one face of said matrix and optionally covering all or part of said membrane. The shielding layer comprises a polymer that does not retain in the stomach more than a conventional dosage form, selected from the group consisting of (a) a hydrophilic polymer which is not instantly soluble in gastric fluids; (b) an enteric polymer substantially insoluble at pH less than 5.5; (c) a hydrophobic polymer; and (d) any mixture of at least two polymers as defined in any of (a), (b) or (c).

By the term "does not prevent biodegradation, bioerosion, dissolution or disintegration of this layer after a predetermined time" is generally meant a period of time of 3–12 hours and up to 24 hours, preferably 8–12 hours, according to the therapeutic need.

The delivery system of the invention comprises a pharmaceutically effective amount of at least one drug, which may optionally be contained in a drug-containing means. The drug may be in the form of raw powder, or soluted, dispersed or embedded in a suitable liquid, semisolid, micro- or nanoparticles, micro- or nanospheres, tablet, capsule or a suitable matrix. The drug, or mixtures of drugs, in any of said forms, may be embedded in at least one layer of the matrix of the delivery system of the invention. Alternatively, in an embodiment having a multi-layered matrix, preferably a bi-layered matrix, the drug may be entrapped between any two of said layers, whether in free form or contained within a drug-containing means. For example, a semi-solid drug may be contained between any two layers of the matrix. Another example is that in which the drug is contained in a tablet, a capsule or any pharmaceutically compatible matrix, and the drug-containing tablet, capsule or pharmaceutically compatible matrix are entrapped between any two layers of the matrix. Such multi-layered embodiments preferably have a shielding layer. Alternatively, the drug, preferably contained with said drug-containing means, may be tethered by tethering means, or otherwise attached, to the delivery system of the invention.

It may be advantageous to further coat the device of the invention with an anti-adhering material, which can be affixed to outer surface/s of the device. Such a material may be any inert, non-swelling material which will prevent self-adhesion of the outer layers (e.g. the matrix or shielding layer) of the device upon hydration thereof. The anti-adhering material may be, for example, cellulose or a cellulose derivative, a silicate, such as magnesium silicate or aluminum silicate, or an enteric polymer substantially insoluble at pH less than 5.5. One preferred example for such a material, used as the anti-adhering layer, is microcrystalline cellulose.

To facilitate administration, the delivery device of the present invention may be administered in a folded configuration. The device is preferably folded into a capsule, preferably a gelatin capsule. In such embodiments it is preferred that the device be further coated with the said pharmaceutically acceptable anti-adhering layer, to prevent its outer layers from adhering to each other when in folded configuration, thus enabling it to unfold during the wetting process in the gastric lumen after administration thereof.

Additionally, folded devices may further comprise a gas-forming agent, not intended for inflation or buoyancy of the device, but rather for providing internal pressure, allowing the folded device to unfold after administration of the capsule and its dissolution in the stomach. The gas-forming agent may be a liquid gas-forming agent which boils at body temperature (34° C.–40° C.), or a solid gas-forming agent. An example for a solid agent is any suitable carbonate, such as calcium carbonate, sodium carbonate or sodium hydrogen carbonate, with sodium hydrogen carbonate being preferred. Liquid gas-forming agents may be methyl formate, tetramethyl silane, iso-pentane, isomers of perfluoropentane, diethyl or diethenyl ether. The gas-forming agent may be in combination with said matrix, or directly or indirectly affixed thereto The delivery device of the invention may further optionally comprise a pharmaceutically acceptable plasticizer. The plasticizer may be contained in any of the parts of the device, for example in the matrix, in the shielding layer or in the membrane. The plasticizer may be any suitable plasticizing agent, as known to the man of the art. For example, the plasticizer may be an ester, such as a phthalate ester, phosphate ester, citrate ester, fatty acid ester and tartarate ester, glycerine or glycol derivatives, or sorbitol. A preferred plasticizer to be contained in the shielding layer is glycerine.

Each of the components of the device may be affixed to other components, to form the device, by any conventional method known to the man of the art of pharmacy and drug design, for example, by heating or melting each layer, or by using compatible conventional adhesive materials, such as α-cyanoacrylates, acrylic or methacrylic adhesives, epoxides or plasticized polyvinyl adhesives. However, 'gluing' of the layers is preferably performed with organic solvents, which slightly dissolve the polymers, such as ethyl alcohol, acetone, methylene chloride, chloroform or carbon tetrachloride.

The hydrophilic polymer suitable for the various components of the delivery system of the invention may be any hydrophilic polymer which, following suitable treatment if necessary, is not instantly soluble in gastric fluids, such as a protein, a polysaccharide, a polyacrylate, a hydrogel or any derivative of these polymers.

Examples of proteins are proteins derived from connective tissues, such as gelatin and collagen, or an albumin such as serum albumin, milk albumin or soy albumin. In preferred embodiments, the hydrophilic polymer is gelatin or a gelatin derivative, preferably enzymatically hydrolyzed gelatin. A specific example is enzymatically hydrolyzed gelatin having a molecular weight of 10,000–12,000.

Examples of suitable polysaccharides are sodium alginate or carboxymethylcellulose.

Other hydrophilic polymers may be polyvinyl alcohol, polyvinyl pyrrolidone or polyacrylates, such as polyhydroxyethylmethacrylate.

The hydrophilic polymer may be cross-linked with a suitable cross-linking agent. Such cross-linking agents are well known to the man of the art of pharmacy and drug design. These may be, for example, aldehydes (e.g. formaldehyde and glutaraldehyde), alcohols, di-, tri- or tetravalent ions (e.g. aluminum, chromium, titanium or zirconium ions), acyl chlorides (e.g. sebacoyl chloride, tetraphthaloyl chloride) or any other suitable cross-linking agent, such as urea, bis-diazobenzidine, phenol-2,4-disulfonyl chloride, 1,5-difluoro -2,4-dinitrobenzene, 3,6-bis-(mercuromethyl)-dioxane urea, dimethyl adipimidate, N,N'-ethylene- bis-(iodoacetamide) or N-acetyl homocysteine thiolactone. Other suitable hydrogels and their suitable cross-linking agents are listed, for example, in the Handbook of Biodegradable Polymers [A. J. Domb, J. Kost & D. M. Weisman, Eds. (1997) Harwood Academic Publishers], incorporated herein by reference. A preferred cross-linking agent is glutaraldehyde.

The enteric polymer is a polymer that is substantially insoluble in a pH of less than 5.5. Such polymers, generally called enteric polymers, are used in the pharmaceutical industry for enteric coating of tables. Examples are shellac, cellulose acetate phthalate, hydroxypropyl methylcellulose phthalate, hydroxypropyl methylcellulose acetate succinate or methylmethacrylate-methacrylic acid copolymers.

There are several advantages in including an enteric polymer in the matrix or the shielding layer, as enteric polymers have improved mechanical properties (e.g. Young's modulus and yield strength). The addition of an enteric polymer to the shielding layer prevented rapid rupture of the shielding layer in vitro A further advantage of using an enteric polymer is to ensure the complete dissolution and/or disintegration of the components of the device, e.g. the matrix, the shielding layer or the membrane, in the intestine, had it not already occurred in the stomach. A preferred enteric polymer incorporated into the shielding layer may be methylmethacrylate-methacrylic acid copolymer, at a ratio of 2:1 ester to free carboxylic groups.

According to a specific embodiment of the invention, the matrix comprises a drug embedded in an enteric polymer. In one such specific embodiment, which comprises the matrix, membrane and a shielding layer, the shielding layer comprises about 50% of the hydrophilic polymer which has been suitably cross-linked to reduce its solubility, about 30% enteric polymer and about 20% plasticizer, preferably glycerine.

The matrix or the shielding layer of the delivery device may contain solely or in combination a degradable or non-degradable hydrophobic polymer.

Examples of non-degradable hydrophobic polymers which may be employed within the delivery device of the invention are ethylcellulose or an acrylic acid-methacrylic acid esters copolymer, having from about 5 to 10% functional quaternary ammonium groups. Other suitable polymers are polyethylene, polyamide, polyvinylchloride, polyvinyl acetate and mixtures thereof. Since such non-degradable polymers do not undergo erosion/degradation, when they are employed in the matrix, the size of the matrix or its mechanical properties should not prevent the device from leaving the stomach.

Examples of degradable hydrophobic polymers are poly (α-hydroxyacids), for example, poly(lactic acid), poly (glycolic acid), copolymers and mixtures of the same.

In embodiments in which the drug is contained in the delivery device, rather than being tethered or attached thereto, the role of the matrix is to contain the drug. In cases where the polymer/polymer mixtures constructing the matrix are not instantly soluble in gastric fluid, the shielding layer is optional, whereas in cases where the drug is embedded in a liquid solution or suspension, in any kind of semisolid such as a gel, ointment or cream or in an instantly soluble polymer film or matrix, which are, in turn, embedded within a layer of the matrix or entrapped between layers of the matrix, the shielding layer becomes essential.

The role of the shielding layer is to maintain the physical integrity of the delivery system (in other words to help in the attachment of the matrix and the membrane), as well as assist in controlling the release rate of the drug from the delivery system. The shielding layer should not by itself control the gastroretentivity of the system, except indirectly, by assisting in the attachment of the matrix to the membrane.

Evidently, all the components of the delivery system of the invention are inert, pharmaceutically compatible substances. By "inert" is meant not reacting with the active drug or affecting its properties in any other manner, or itself producing a biological or other effect, particularly adverse effect, upon administration to the treated subject. By "pharmaceutically compatible" is meant not producing a biological or other effect particularly adverse effect upon administration to the treated subject.

The delivery system of the invention comprises a pharmaceutically effective amount of at least one active drug. This amount, for purposes herein, is that determined by such considerations as are known in the art, and generally means an amount sufficient to prevent, alleviate, treat or cure a disease or disorder The active agent may be incorporated within the matrix (as a powder, solution, dispersion or any other suitable form) or in combination therewith. By the term "embedded within the matrix" is meant any such incorporation or combination of the drug with the matrix. The active drug embedded in the matrix may be in combination with suitable carriers, diluents and adjuvants, all being inert, non-toxic solid or liquid substances which assist in the delivery of the drug to the target tissue or organ.

The drug-containing layer (medicament reservoir) may be in the form of a continuous or non-continuous matrix or hydrogel, which contains the drug in solution, dispersion or both. Optionally, the drug can be first incorporated into controlled release micro- or nanoparticles or micro- or nanospheres, to be combined with the matrix or hydrogel. The drug can be incorporated in any kind of semisolid such as a gel, ointment or cream or directly be contained in a tablet or a capsule, and the drug-containing tablet or capsule embedded into the matrix, or the drug-containing tablet or capsule can be tethered to or attached to the said delivery system (in this embodiment the matrix of the device may optionally comprise another drug or drugs). The tablet or capsule can be tethered by any pharmaceutically acceptable tethering means, such as, for example, degradable or non-degradable threads, including contrast threads.

The active drug according to the invention may be any drug suitable for preventing, alleviating, treating or curing a disease or disorder within the gastrointestinal tract.

The drug may be a drug having a narrow absorption window in the gastrointestinal tract. Examples of drugs having a narrow absorption window in the gastrointestinal tract are therapeutic nucleic acid sequences or derivatives, amino acid sequences or derivatives, peptidomimetic drugs, antibiotic agents, therapeutic ions, vitamins, bronchodilators, anti-hypertensive agents, diuretic agents, anti-gout agents, anti-hyperlipidemic agents or ACE inhibitors.

Therapeutic nucleic acid derivatives are, for example, acyclovir, AZT or didanosine.

Examples of therapeutic amino acid sequences or their derivatives are gabapentin, levodopa, α-methyldopa, baclofen or valacyclovir.

Examples of antibiotic agents having a narrow absorption window are nitrofurantoin, ciprofloxacin or β-lactam antibiotic agents such as amoxycillin or cephalexin.

Examples of therapeutic ions are lithium carbonate or citrate, calcium carbonate or citrate.

Examples of vitamins are riboflavin, ascorbic acid, folic acid or vitamin E.

The anti-hyperlipidemic agent may be pravastatin.

Examples of ACE inhibitors are captopril, benazepril, enalapril, cilazapril, fosinopril or ramipril.

Examples of bronchodilators are albuterol or pirbuterol.

Other examples of drugs having a narrow absorption window in the gastrointestinal tract are furosemide, allopurinol or atenolol.

In addition to drugs having a narrow absorption window in the gastrointestinal tract, the delivery system of the invention may comprise a drug for local treatment of the gastrointestinal tract. These may be used, for example, in the treatment of neoplasms of the stomach, such as adenocarcinoma of the stomach or gastric lymphoma.

Examples of drugs for the local treatment of the gastrointestinal tract are anti-tumor agents, histamine (H2) blockers, bismuth salts, synthetic prostaglandins or antibiotic agents.

H2 blockers may be cimetidine, famotidine or ranitidine.

Bismuth salts may be bismuth subsalicylate or bismuth subcitrate.

An example of a synthetic prostaglandin is misoprostol.

The anti-tumor drug may be 5-fluorouracil, doxorubicin, mitomycin, semustine, cisplatin, etoposide or methotrexate.

Suitable antibiotic agents may be clarithromycin, amoxycillin, metronidazole or a tetracycline.

In addition to the above drugs, which have a narrow absorption window in the gastrointestinal tract or which are intended to local treatment of the gastrointestinal tract, the delivery device of the invention may contain as the active agent a drug which degrades in the colon, for example, metoprolol.

Any agent having a therapeutic effect in the gastrointestinal tract, or which has a narrow absorption window in the gastrointestinal tract or which degrades in the colon, other than the aforementioned agents, may be delivered by the device of the invention. Such agents are well known to the man of the art and may be delivered alone or in combination with other suitable therapeutic agents.

One example of a device of the invention is illustrated in FIG. 1. The device (1) comprises a matrix (100) having a three dimensional configuration, containing the drug. Strips (110), are affixed to the sides of the three dimensional matrix (100), forming a continuous membrane (also referred to as frame) having mechanical strength. The strips (110) are adjacent to each other and the drug-containing matrix is framed within them. The device further comprises shielding layers (120), covered on their exposed faces by anti-adhering powder layers (130).

Figure 2:
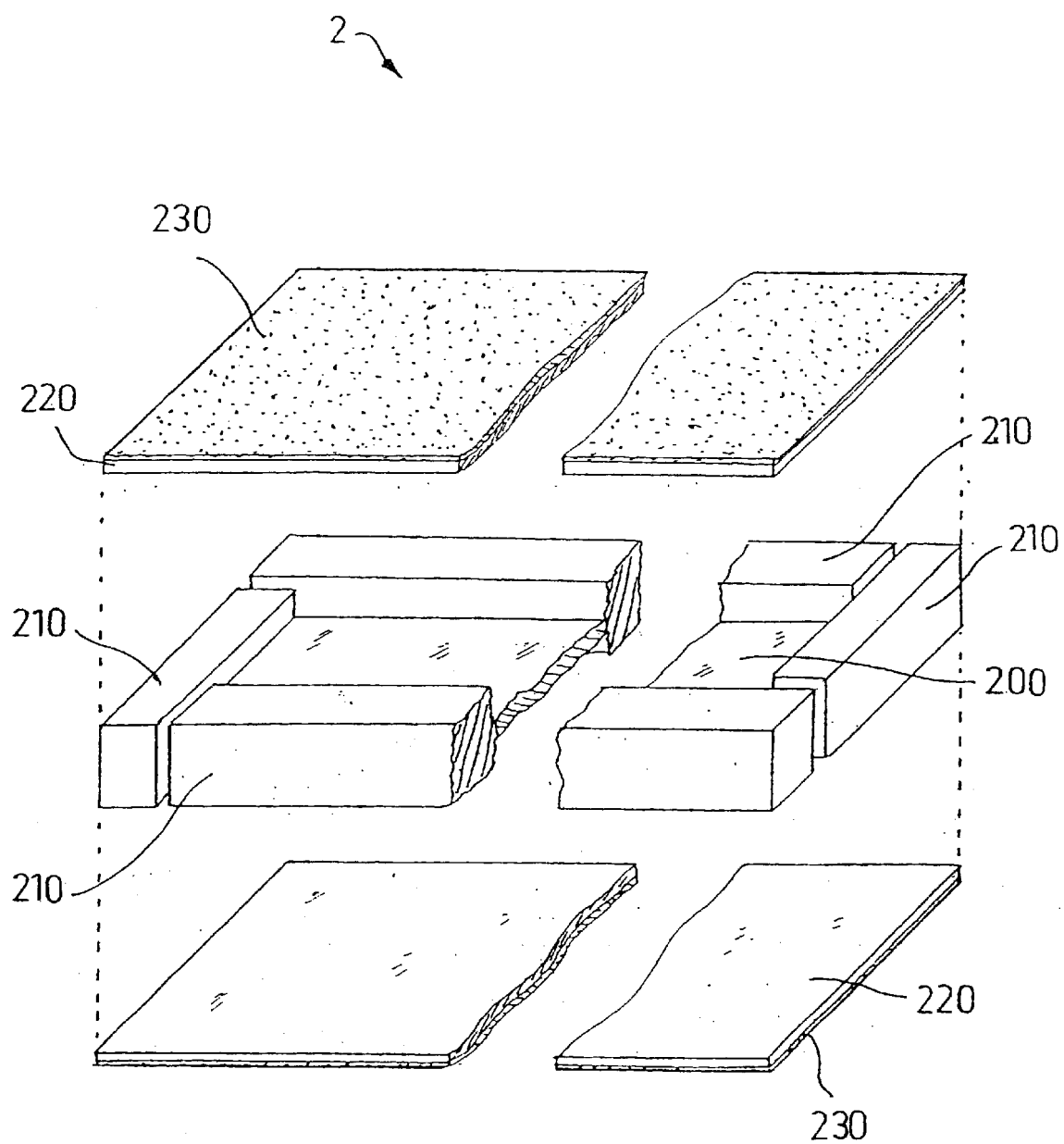
FIG. 2 is a partially fragmented exploded perspective view of a modification of the embodiment shown in FIG. 1.

An alternative device (2) is illustrated in FIG. 2. As can be seen from the Figure, the strips (210) are affixed to the drug-containing matrix with gaps therebetween, forming a non-continuous frame.

Figure 3:
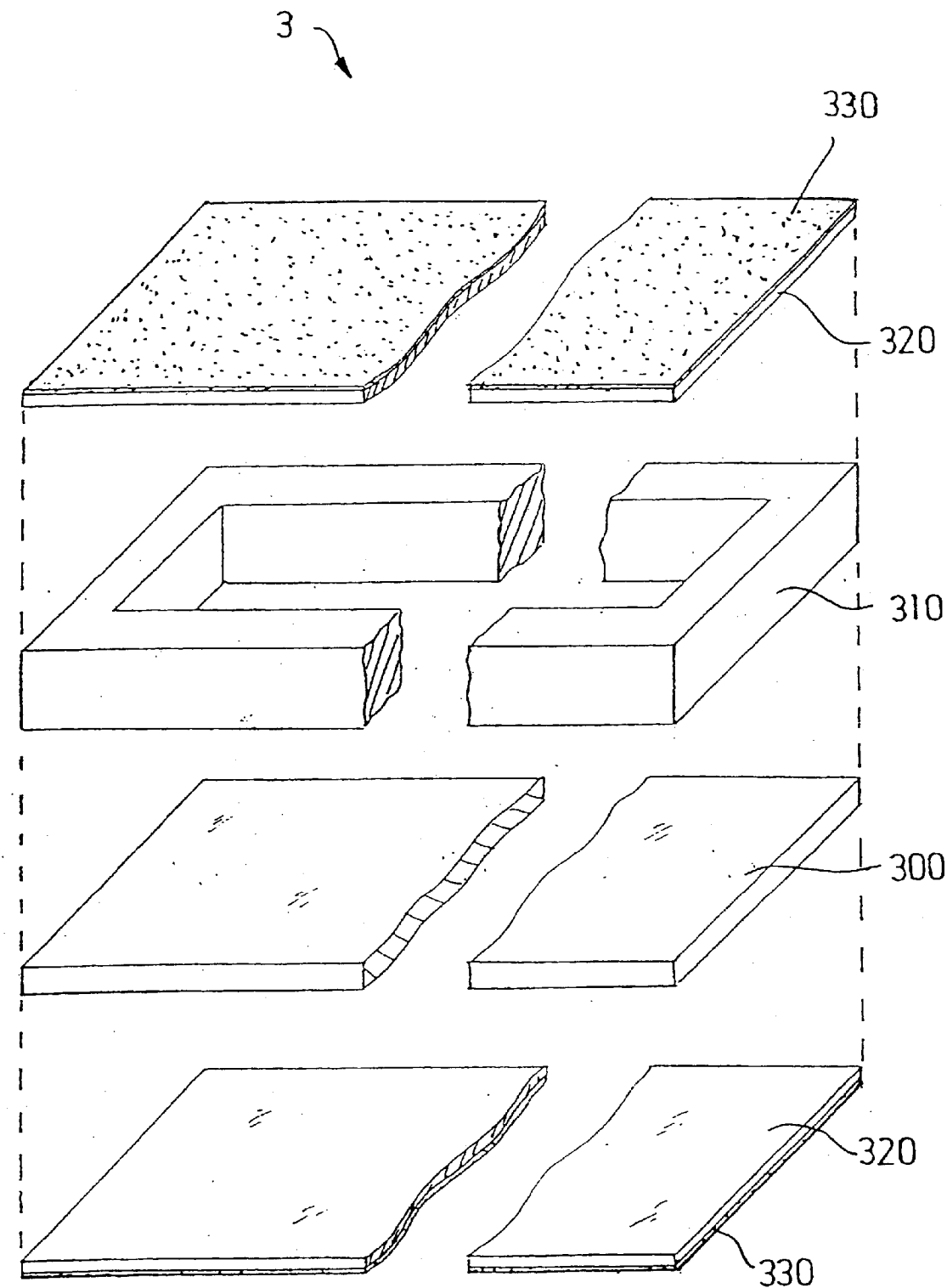
FIG. 3 is a partially fragmented exploded perspective view of another embodiment of a device according to the present invention.

Another embodiment is illustrated in FIG. 3. In this embodiment (3), the membrane (310) is comprised of one unit only. It is affixed to the top of the drug-containing matrix (300). Alternatively, the membrane (frame) may be fragmented-continuous as illustrated in the frame of FIG. 1, or non-continuous in a manner similar to the frame of FIG. 2. Shielding layers (320) are affixed to the bottom of the matrix (300) and onto top of the membrane (310) and matrix. Anti-adhering powder layers (330) are affixed to the exposed faces of the shielding layers. The shielding layers thus sandwich the drug-containing matrix and the mechanically strong membranes affixed thereto.

It should be noted that the membrane, whether continuous or non-continuous, fragmented or non-fragment, is not limited to the embodiments presented in FIGS. 1 to 3. Thus, the membrane may have a continuous or non-continuous, fragmented or non-fragmented circular, multi-lobed or cross-shaped configuration. These continuous or non-continuous, fragmented or non-fragmented membranes may be comprised of degradable polymer/s, non-degradable polymer/s or mixtures thereof, and due to its high mechanical properties, is intended to prevent the stomach from rapidly diminishing the size of the device, by its natural mechanical activity, which includes contractions, to a size which will enable rapid passage of the device to the intestine. The membrane may be incorporated into any suitable part of the delivery system, for example, into all or part of the frame, and may have a symmetric or asymmetric configuration. The membrane may be incorporated also in specific parts of the delivery system other than the frame.

Gastrointestinal-associated diseases and disorders which may be prevented, alleviated, treated or cured using the delivery system of the invention may include, but are not limited to, peptic ulcer, nonulcer dyspepsia, Zollinger-Ellison syndrome, gastritis, duodenitis and the associated ulcerative lesions, stomach or duodenum neoplasms. Evidently, the device of the invention may be employed for any other disorder associated with the gastrointestinal tract, as determined by such considerations known to the man of the art.

The device of the invention may have numerous two or three dimensional configurations, such as a disc, a multi-lobed configuration, a triangle or a quadrangle and may be planar or non-planar. When the device has a rectangle geometry, it has preferably surface area and thickness of about 2–8 cm×1.5–5 cm and 0.1–3 mm, respectively. Preferably the surface area is 5 cm×2.5 cm and the thickness 0.9 mm.

It is not necessary that the drug or medicament reservoir be uniformly distributed in the inner matrix. For example, if the device has a multi-lobed configuration, it is possible that only some lobes contain the drug or medicament reservoir. Further, the active agent may be incorporated into only one lobe (or into only a part of any other form of the device) as a tablet affixed thereto.

The matrix preferably has the dimensions of about 0.5–7.0 cm×0.5–4 cm, more preferably 4 cm×1.5 cm.

The dimensions of the strips forming the membrane are preferably 0.5–7.0 cm×0.1–1.0 cm, with a thickness of 0.05–2.5 mm, more preferably 2–4.5 cm×0.5 cm, with a thickness of 0.65 mm.

The dimensions of the shielding layers are preferably 2–8 cm×1.5–5 cm, and more preferably 5 cm×2.5 cm.

As the surface area of the device is substantially large for easy and convenient swallowing, it may be folded or rolled into a suitable carrier, such as a pharmaceutically acceptable capsule. After reaching the stomach, the carrier dissolves and the device unfolds to its original size, resulting in its retention in the stomach for the desired, prolonged period of time. The drug is then released in a controlled manner in the target site.

The invention will be described in more detail on hand of the following Examples, which are illustrative only and do not in any sense limit the invention, which is defined by the appended claims.

EXAMPLE

Materials and Methods

Glycerine, ethyl alcohol and methylene chloride were purchased from Frutarom; enzymatically hydrolyzed gelatin with average molecular weight of 10,000–12,000 was purchased from Croda; hexanesulfonic acid was purchased from BDH; methylmethacrylate-methacrylic acid copolymers were provided from Rhom Pharma; 1-PLA with Mw of 427,000 and Mn of 224,500 was purchased from Boehringer Ingelheim; triethyl citrate was provided by Morflex; ethylcellulose was provided by Teva; polyvinyl pyrrolidone was provided by Taro; glutaraldehyde 25% and acetonitrile were purchased from Merck; chloroform, orthophosphoric acid and trichloroacetic acid were purchased from Baker. All solvents were of analytical grade, except acetonitrile which was HPLC grade.

The layers of the exemplified devices were prepared by casting the suitable polymer solutions and evaporating the solvents at 37° C. or in a laminar hood at ambient temperature. In the preparation of the 1-PLA and ethylcellulose-containing layer, chloroform was used as the solvent.

A mixture of 50% ethyl alcohol and 50% NaOH—$K_2HPO_4$ buffer (pH 12.7) was employed as a solvent for the preparation of the outer layers (shielding layers), in particular, for those comprising a mixture of a hydrophilic polymer and an enteric polymer.

Example 1

Riboflavin-containing Pharmaceutical Devices

A disc of 9.5 cm diameter containing riboflavin (30%) in combination with shellac (70%) was prepared by dissolving shellac in ethyl alcohol (1:10) and dispersing riboflavin in the same. The mixture was then cast and the solvent removed by evaporation at 37° C. The dry disc was cut into a 5 cm×2.5 cm segment.

The cast was then sandwiched within two identical intermediate layers (the shielding layers) prepared by mixing enzymatically hydrolyzed gelatin (48%, average molecular weight 10,000–12,000), methylmethacrylate-methacrylic acid copolymer in a ratio of ester to free carboxylic groups of 2:1 (30%) and glycerine (20%) in a mixture of 50% ethyl alcohol and 50% NaOH—$K_2HPO_4$ buffer. Glutaraldehyde (2%), diluted in the same solvent, was added whilst mixing, promptly before casting for cross-linking and evaporation. Contrast threads (0.5 cm long) were added to the cast before final evaporation of the solvent, to allow roentgenographic detection of the device after administration.

The resulting layers were then coated with a thin (outer) layer of microcrystalline cellulose powder (the anti-adhering agent).

In principle, each layer, i.e. the riboflavine-containing layer (the inner layer), the intermediate (shielding) layers and the outer layers, were affixed by applying thereto a solution of ethyl alcohol and allowing the same to dry, such that the intermediate layers were affixed onto the surface of the inner layer, and the microcrystalline cellulose (outer) layers onto the intermediate layers.

The resulting device had a rectangular configuration of about 5 cm×2.5 cm×0.75 mm.

A rectangular drug-containing layer (the inner layer) was prepared as described in A, was cut into a 4 cm×1.5 cm segment, and was continuously framed with four 0.5 cm-wide strips (4.5 cm and 2 cm long), containing 1-PLA (90%) and ethyl cellulose (10%) previously dissolved in chloroform and cast. The resulting frame, with no gaps between the strips, provided the device with some degree of mechanical strength. The strips contained threads of a contrast material (the longer strips contained two threads while the shorter strips contained only a single thread).

An intermediate layer (shielding layer) was prepared as described in A. The inner layer was affixed to a shielding layer by applying thereto a solution of ethyl alcohol.

The frame was adhered on the sides of the shielding layer using minute amounts of methylene chloride, which was then evaporated.

The second shielding layer was adhered to the inner layer and the frame using the mentioned solvents, i.e. ethyl alcohol and minute amounts of methylene chloride, respectively.

In this embodiment, one of the shielding layers contained three contrast threads. The longer strips contained two contrast threads each, while the shorter strips contained one contrast thread each.

Then, the intermediate layers were coated with microcrystalline cellulose adhered thereto using ethyl alcohol.

The same principles were used to prepare devices with different characteristics, e.g. thickness of plastic membrane;

plastic membrane polymeric constitution; size of device; and size, number and continuity of plastic strips.

Example 2

In Vivo Assessment of the Effect of Different Properties of Gastroretentive Dosage form (GRDF) on its Transit Time in the Stomach Beagle dogs (six) were fasted for at least 18 hours before being administered with a delivery device (#1-#8). Water was given to the dogs ad libitum. Each dog then received orally, through a gastric tube, 400 ml of buffer (HCl—KCl, pH 1.5), and subsequently the device, folded into a gelatin capsule (000). The experiment was repeated with six dogs for each of the devices.

Device #1

The two outer membranes (shielding layers) were identical and were constituted from 48% enzymatically hydrolyzed gelatin with average molecular weight 10,000–12,000, 30% methylmethacrylate-methacrylic acid copolymer at a ratio of ester to free carboxylic groups of 2:1, 20% glycerine and 2% glutaraldehyde, and were covered with a thin layer of microcrystalline cellulose powder.

The matrix comprised 70% shellac and 30% riboflavin.

The thickness of each shielding layer and of the matrix was 0.135 mm and 0.5 mm, respectively. The size of the matrix and of the shielding layers which cover the matrix, and therefore of the device, was 5 cm×2.5 cm.

One of the shielding layers contained nine contrast threads which were 0.5 cm long each.

The gluing of all membranes and the microcrystalline cellulose layer was by ethyl alcohol.

Device #2

The size of the matrix which had the same constitution as in device #1 was 4 cm×1.5 cm. The two shielding layers were as in device #1.

The matrix had a frame of four plastic strips of a mixture of 90% 1-PLA-10% ethylcellulose. The width of the strips was 0.5 cm. The length of each two strips was 4.5 cm and 2 cm. The thickness of the strips was 0.65 mm.

The longer strips contained two contrast threads each, while the shorter strips contained one contrast thread each. One of the shielding layers contained three contrast threads.

Gluing the shielding layers to the matrix and the microcrystalline cellulose layer was with ethyl alcohol, while the plastic membrane was adhered using methylene chloride.

Device #3

The two shielding layers, the matrix and their sizes were as in device #2.

All plastic strips are in the frame of the matrix. Two plastic strips in each side of the longer dimension were in a length of 2.1 cm (altogether four strips). Two plastic strips, one in each side of the shorter dimension, had the same length as in device #2 (2 cm). The thickness of the strips was as in device #2 (0.65 mm). There was a distinct gap of 2 mm between each of the six plastic strips.

Each of the plastic strips contained one contrast thread. One of the shielding layers contained three contrast threads.

The gluing of all layers was as device #2.

Device #4

The two shielding layers, the matrix and their sizes were as in device #2.

All twelve plastic strips were in the frame of the matrix. Two and four plastic strips in each side of the shorter and longer dimensions of the frame, respectively, were all of the size of 0.5 cm×1 cm. The thickness of the strips was as device #2. There was a distinct gap of 2 mm between each of the twelve plastic strips Each of the plastic strips contained one contrast thread. One of the shielding layers contained three contrast threads.

The gluing of all layers was as in device #2.

Device #5

The shielding layers, the matrix and the strips were identical in their constituents to device #2.

The size of the matrix was 1.5 cm×1.5 cm. The size of the four plastic strips was 0.5 cm×2 cm. The thickness of the strips was as device #2. All plastic strips were in the frame of the matrix. The size of the shielding layers, which cover the matrix and the strips (and therefore is the size of the device) was 2.5 cm×2.5 cm.

Each strip and one of the shielding layers contained one 0.5 cm long contrast thread.

The gluing of all layers was as device #2.

Device #6

The shielding layers, the matrix and their sizes were as in device #2.

The plastic strips were constituted from 97% ethylcellulose-3% triethyl citrate, previously dissolved in methylene chloride and cast. The strips which were in the frame of the matrix were identical in their sizes and thickness to the plastic strips in device #2.

The contrast threads and the gluing of all layers were as device #2.

Device #7

Device #7 was similar to device #2, but for the thickness of the plastic strips which was 0.2 mm.

Device #8

Tablets which were constituted from 98% ethylcellulose-2% polyvinyl pyrrolidone were prepared using the wet granulation method. The dimensions of the tablets were 0.8 cm diameter and 0.35 cm thickness.

Each tablet contained two 0.5 cm long contrast threads, positioned perpendicularly one to the other.

X-ray pictures were then taken after 1, 2, 4, 6, 8 and 13 hours. The results of the GRTs are given in Table 1.

TABLE 1

| | Number of Devices (out of 6) Retained in Stomach | | | | | | |
|---|---|---|---|---|---|---|---|
| | Time (hrs.) | | | | | | |
| Device # | 0 | 1 | 2 | 4 | 6 | 8 | 13 |
| 1 | 6 | 6 | 3 | 2 | 1 | 0 | 0 |
| 2 | 6 | 6 | 6 | 6 | 6 | 6 | 6 |
| 3 | 6 | 6 | 6 | 6 | 6 | 5 | 4 |
| 4 | 6 | 6 | 6 | 5 | 4 | 4 | 4 |
| 5 | 6 | 6 | 6 | 6 | 5 | 5 | 5 |
| 6 | 6 | 6 | 6 | 6 | 5 | 4 | 3 |
| 7 | 6 | 6 | 6 | 6 | 5 | 5 | 5 |
| 8 | 6 | 6 | 5 | 2 | 0 | | |

Example 3

Effect of Sustained Release of Riboflavin via GRDF on its Bioavailability, and Pharmaconkinetic Profile in Comparison to Bolus Oral and Intravenous Modes of Administration In order to assess the effect of the mode of administration on riboflavin bioavailability, Beagle dogs (n=6) were deprived of food for at least 18 hr (with water available ad libitum) received 100 mg riboflavin-5-phosphate (flavine mononucleotide) by 3 different modes of administration: (1) 5 ml of sterile isotonic solution of the drug given by intravenous bolus, in addition to concurrent oral administration of 400 ml buffer solution (HCl—KCl, pH=1.5) delivered to the stomach by a gastric tube; (2) per-oral bolus solution of the drug in 400 ml of the same acidic buffer solution; (3) GRDF (a device similar to device #2 as described in Example 2, except that the matrix layer was constituted from shellac:riboflavin-5-phosphate at a ratio of 5.5:4.5) was administered to the stomach within a gelatin capsule with 400 ml of the same buffer solution and released the drug in a sustained release manner. Each dog received the drug by each of these modes, with at least one-week washout period between every phase of the study.

Following each administration blood samples (4 ml) were collected into 5 ml heparinized test tubes wrapped in aluminum foil (to protect from light), for modes (1) and (2) at times 0, 0.25, 0.5, 1, 1.5, 2, 2.5, 3, 3.5, 4, 6, 8, 11, 24 hours, and for mode (3) at times 0, 0.5, 1, 1.5, 2, 25, 3, 4, 6, 9, 12, 15, 18, 21, 24, 27, 30, 33, 36 and 48 hours. Plasma was separated following centrifugation (4000 rpm for 10 minutes), and stored at −20° C. pending analysis.

Following the GRDF administration (mode 3) X-ray pictures were taken at 4, 6, 8, 12, 24, 36 and 48 hours, to ascertain the location of the delivery system. The dogs were allowed to eat 24 hrs after the beginning of the experiment.

Riboflavin plasma concentrations were determined by an HPLC method as follows: 100 μl trichloroacetic acid (20%) was mixed with 300 μl of a plasma sample. Following centrifugation of the mixture (13,000 rpm for 10 minutes) the supernatant was separated and incubated for 10 min at 85° C. After additional centrifugation (13,000 rpm for 10 minutes) 60 μl of the solution were injected to C18 HPLC column, with mobile phase that consisted of 15% acetonitrile in solution A (10 mmol potassium dihydrogen phosphate/L and 5 mmol hexanesulfonic acid/L, brought to a pH of 3 with orthophosphoric acid) at a flow rate of 1 ml/min. A spectrofluorometric detector set at 445 nm for excitation wavelength and 530 nm for emission wavelength detected the drug. Drug concentrations were determined with appropriate standard curves. In mode 3, X-ray pictures showed that all devices were still present in the stomach of the six dogs after 48 hours.

Figure 4:
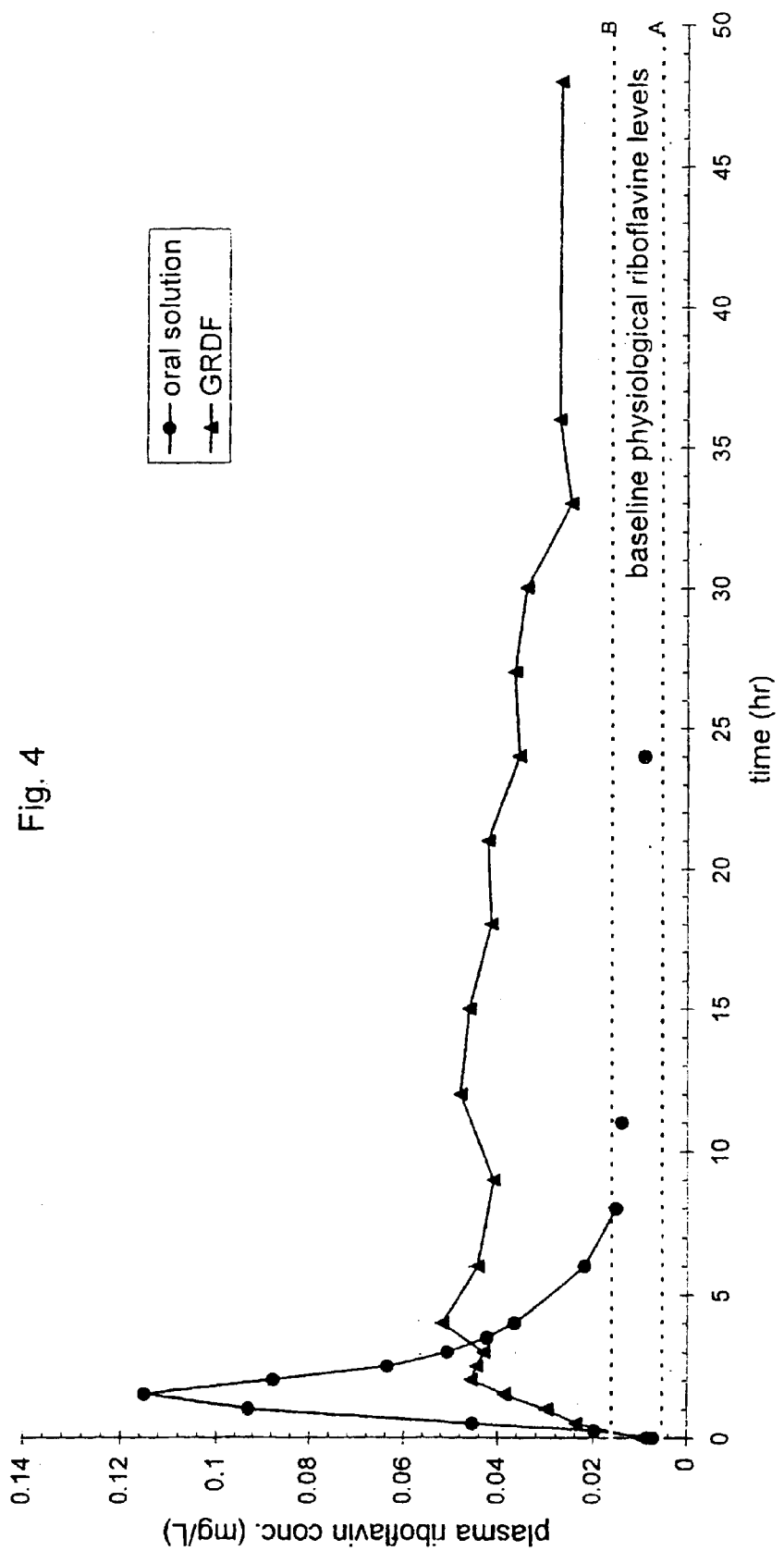
FIG. 4 shows the effect of mode of administration of 100 mg riboflavin-5-phosphate on mean riboflavin plasma concentrations in dogs. Drug given either as IV bolus, oral solution or gastroretentive dosage form (GRDF) (6 dogs). Concentrations between the dotted lines A and B represent baseline physiological riboflavin levels.

The plots of plasma riboflavin concentrations vs. time detected in the dogs following the administration of 100 mg riboflavin-5-phosphate by the three modes of administration are presented in FIGS. 4 and 5.

The slopes of the log-terminal slope following the three modes of administration were 0.44±0.13, 0.35±0.14 and 0.021±0.014 $hr^{-1}$ for intravenous, oral solution and GRDF, respectively. According to these results (no statistically significant differences between iv and PO data) it can be concluded that the rate of riboflavin elimination is 0.4 $hr^{-1}$ (as found following both iv and PO administration). This finding also verifies that the rate of riboflavin absorption is faster than the rate of elimination. On the other hand, the fact that the log-terminal slope following the GRDF administration is considerably slower than the elimination process indicates that it is a flip-flop kinetics, and this slope represents the absorption rate constant of riboflavin in this case, thereby confirming the sustained release pattern of the drug from the GRDF is the rate-limiting step in the absorption process.

The absolute bioavailability of riboflavin following oral administration was found to be 5.8±2.2%. By calculating the fractional AUC values of times zero to 48 hours, normalized by the intravenous AUC values, it is concluded that the GRDF increases the bioavailability of riboflavin well over 3.5-fold, as apparent from the pharmacokinetic profile obtained for the GRDF in comparison to the other modes of administration (FIGS. 4 and 5).

What is claimed is:

1. A foldable pharmaceutical gastroretentive drug delivery system for the controlled release of an active agent in the gastrointestinal tract, which system comprises:
    a) a single- or multi-layered matrix having a two- or three-dimensional geometric configuration comprising a polymer that does not retain in the stomach more than a conventional dosage form, said polymer selected from the group consisting of:
        (1) a degradable polymer selected from:
            (i) a hydrophilic polymer which is not instantly soluble in gastric fluids;
            (ii) an enteric polymer substantially insoluble at pH less than 5.5;
            (iii) a hydrophobic polymer; and
            (iv) any mixture of at least two polymers as defined in (i), (ii) or (iii);
        (2) a non-degradable polymer; and
        (3) a mixture of at least one polymer as defined in (1) with at least one polymer as defined in (2);
    b) a continuous or non-continuous membrane, that does not retain in the stomach more than a conventional dosage form, affixed or attached to said matrix, said membrane comprising at least one polymer having a substantial mechanical strength; and
    c) a drug, which may be in a particulate form or optionally contained within a drug-containing means;
        said drug or drug contained within said drug-containing means being embedded in a layer of said matrix, or being entrapped between at least two layers of said matrix, or being attached to said delivery system,
        wherein said matrix when affixed or attached to said membrane prevents evacuation from the stomach of said delivery system for a period of time of from about 3 to about 24 hours.

2. The delivery system as claimed in claim 1, further comprising a shielding layer covering at least one face of said matrix, optionally covering all or part of said membrane, said shielding layer comprising a polymer that does not retain in the stomach more than a conventional dosage form, said polymer being selected from the group consisting of:
    (a) a hydrophilic polymer which is not instantly soluble in gastric fluids;
    (b) an enteric polymer substantially insoluble at pH less than 5.5;
    (c) a hydrophobic polymer; and
    (d) any mixture of at least two polymers as defined in any of (a), (b) or (c).

3. A drug delivery system as claimed in claim 1 or 2, wherein said drug is in the form selected from the group consisting of a raw powder, a powder soluted, dispersed or embedded in a suitable liquid, semisolid, micro- or nanoparticles, micro- or nanospheres, a tablet, a capsule or a suitable specific two- or three-dimensional matrix.

4. The delivery system as claimed in claim 1, further comprising a suitable plasticizer.

5. The delivery system as claimed in claim 4, wherein said plasticizer is contained in said shielding layer.

6. The delivery system as claimed in claim 1, further comprising at least one gas-forming agent.

7. The delivery system as claimed in claim 1, further comprising an anti-adhering layer affixed to at least one outer face thereof.

8. The delivery system as claimed in claim 1, wherein said hydrophilic polymer is selected from the group consisting of a protein, a polysaccharide, a polyacrylate, a hydrogel, polyvinyl alcohol or polyvinyl pyrrolidone, or a derivative of such hydrophilic polymers.

9. The delivery system as claimed in claim 1, wherein said enteric polymer is selected from the group consisting of shellac, cellulose acetate phthalate, hydroxypropyl methylcellulose phthalate, hydroxypropyl methylcellulose acetate succinate or methylmethacrylate- methacrylic acid copolymers.

10. The delivery system as claimed in claim 2, wherein said shielding layer comprises a mixture of said hydrophilic polymer and said enteric polymer.

11. The delivery system as claimed in claim 10, wherein said hydrophilic polymer is cross-linked with a suitable cross-linking agent.

12. The delivery system as claimed in claim 11, wherein said cross-linking agent is glutaraldehyde.

13. The delivery system as claimed in claim 11, wherein said hydrophilic polymer is an enzymatically hydrolyzed cross-linked gelatin or derivative thereof.

14. The delivery system as claimed in claim 11, wherein said enteric polymer is methylmethacrylate-methacrylic acid copolymer having a ratio of ester to free carboxylic groups of 2:1.

15. The delivery system as claimed in claim 1, wherein said hydrophobic non-degradable polymer is selected from the group consisting of ethylcellulose, a copolymer of acrylic acid and methacrylic acid esters, having from about 5 to 10% functional quaternary ammonium groups, polyethylene, polyamide, polyvinylchloride, polyvinyl acetate or mixtures thereof.

16. The delivery system as claimed in claim 1, wherein said membrane is selected from the group consisting of hydrophobic non-degradable polymer/s, hydrophobic degradable polymer/s1 or mixtures thereof.

17. The delivery system as claimed in claim 16, wherein said membrane is comprised of a mixture of 1-poly(lactic acid) (1-PLA) and ethylcellulose at a ratio of 9:1, respectively.

18. The delivery system as claimed in claim 7, wherein said anti-adhering layer is selected from the group consisting of a pharmaceutically acceptable cellulose or derivative thereof, silicate or an enteric polymer substantially insoluble at pH less than 5.5.

19. The delivery system as claimed in claim 18, wherein said anti-adhering layer is microcrystalline cellulose.

20. The delivery system as claimed in claim 4, wherein said plasticizer is an ester selected from the group consisting of phthalate esters, phosphate esters, citrate esters, fatty acid esters and tartarate esters, glycerine or glycol derivatives, or sorbitol.

21. The delivery system of claim 10, wherein said plasticizer is glycerine.

22. The delivery system as claimed in claim 6, wherein said gas-forming agent is a liquid gas-forming agent which boils at body temperature or a solid gas-forming agent.

23. The delivery system as claimed in claim 1, having a form selected from the group consisting of a disc, multilobed configuration, a triangle or a quadrangle, said system being planar or non-planar.

24. The delivery system as claimed in claim 1, being folded into a suitable capsule.

25. A capsule containing a delivery system as claimed in claim 1.

26. The delivery system as claimed in claim 1, wherein said drug is a drug having a narrow absorption window in the gastrointestinal tract.

27. The delivery system as claimed in claim 26, wherein said drug is selected from the group consisting of a therapeutic nucleic acid or amino acid sequence, a nucleic acid or amino acid derivative, a peptidomimetic drug, an antibiotic, a therapeutic ion, a vitamin, a bronchodilator, an anti-gout agent, an anti-hypertensive agent, a diuretic agent, an anti-hyperlipidemic agent or an ACE inhibitor.

28. The delivery system as claimed in claim 1, wherein said drug is a drug for local treatment of the gastrointestinal tract.

29. The delivery system as claimed in claim 28, wherein said drug is selected from the group consisting of an anti-tumor agent, a histamine (H2) blocker, a bismuth salt, a synthetic prostaglandin or an antibiotic agent.

30. The delivery system as claimed in claim 1, wherein said active agent degrades in the colon.

31. The delivery system as claimed in claim 1, wherein said drug delivery system is administered to a mammal for the treatment of gastrointestinal associated disorders selected from the group consisting of peptic ulcer, nonulcer dyspepsia, Zollinger-Ellison syndrome, gastritis, duodenitis and the associated ulcerative lesions, stomach or duodenum neoplasms.

32. The delivery system as claimed in claim 9 having a ratio of ester to free carboxylic groups of 2:1.

33. The delivery system as claimed in claim 10 further comprising a plasticizer.

34. The delivery system as claimed in claim 22 wherein said solid gas-forming agent comprises a pharmaceutically acceptable carbonate.

35. The delivery system as claimed in claim 30 wherein said active agent comprises metopolol.

* * * * *

UNITED STATES PATENT AND TRADEMARK OFFICE
CERTIFICATE OF CORRECTION

PATENT NO.   : 6,685,962 B2
DATED        : February 3, 2004
INVENTOR(S)  : Michael Friedman et al.

It is certified that error appears in the above-identified patent and that said Letters Patent is hereby corrected as shown below:

<u>Column 19,</u>
Line 40, delete "polymer/sl" and insert therefor -- polymer/s, --.

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,685,962 B2
DATED         : February 3, 2004
INVENTOR(S)   : Michael Friedman et al.

It is certified that error appears in the above-identified patent and that said Letters Patent is hereby corrected as shown below:

Column 8,
Line 67, after "thereto" insert -- . --.

Column 10,
Line 3, after "vitro" insert -- . --.

Column 14,
Line 8, at the beginning of the line, insert -- A. --.
Line 39, at the beginning of the line, insert -- B. --.

Signed and Sealed this

Third Day of August, 2004

JON W. DUDAS
*Acting Director of the United States Patent and Trademark Office*